United States Patent [19]

Gallo et al.

[11] Patent Number: 5,129,877
[45] Date of Patent: Jul. 14, 1992

[54] RECEPTOR-MEDIATED DELIVERY SYSTEM

[75] Inventors: James M. Gallo; Emad E. Hassan, both of Athens, Ga.

[73] Assignee: University of Georgia Research Foundation, Inc., Athens, Ga.

[21] Appl. No.: 582,998

[22] Filed: Sep. 14, 1990

Related U.S. Application Data

[63] Continuation of Ser. No. 188,358, Apr. 29, 1988, abandoned.

[51] Int. Cl.⁵ ..................... A61M 37/00; A61K 37/22
[52] U.S. Cl. ................................. 600/12; 424/450
[58] Field of Search ................. 600/6, 12; 424/1.1, 424/4, 9, 450, 488, 499; 128/653 CA

[56] References Cited

U.S. PATENT DOCUMENTS

| | | | |
|---|---|---|---|
| 3,474,777 | 10/1969 | Figge et al. | |
| 4,157,323 | 6/1979 | Yen et al. | 260/29.7 M |
| 4,285,819 | 8/1981 | Yen et al. | 210/679 |
| 4,331,654 | 5/1982 | Morris | 600/12 |
| 4,501,726 | 2/1985 | Schröder et al. | 600/12 |
| 4,582,622 | 4/1986 | Ikeda et al. | 436/526 |
| 4,612,247 | 9/1986 | Walsh et al. | 210/688 |
| 4,637,929 | 1/1987 | Quay | 128/654 |
| 4,639,364 | 1/1987 | Hoey | 128/654 |
| 4,647,447 | 3/1987 | Gries et al. | 424/9 |
| 4,647,536 | 3/1987 | Mosbach et al. | 435/177 |
| 4,652,257 | 3/1987 | Chang | 600/12 |
| 4,656,026 | 4/1987 | Coffman et al. | 128/654 |
| 4,669,481 | 6/1987 | Eisenberg et al. | 128/654 |
| 4,687,748 | 8/1987 | Schröder | 435/7 |
| 4,713,249 | 12/1987 | Schröder | 424/488 |
| 4,758,422 | 7/1988 | Quay | 424/9 |
| 4,772,475 | 9/1988 | Fukui et al. | 424/488 |
| 4,803,168 | 2/1989 | Garvis, Jr. | 435/178 |
| 4,827,945 | 5/1989 | Groman et al. | 128/653 R |
| 4,853,226 | 8/1989 | Machida et al. | 424/499 |

OTHER PUBLICATIONS

Zubay, Geoffrey, *Biochemistry*, (1983), pp. 645–656.
Widder et al., *Proc. Soc. Exper. Biol. Med.*, 58, 141–146 (1978).
Allan et al., "Biomedical Applications of Chitin and Chitosan", pp. 119–113, *Chitin, Chitosan and Related Enzymes*, (Academic Press, Inc., New York, 1984).
Nagai, et al., "Application of Citin and Chitosan to Pharmaceutical Preparations", pp. 21–39, *Chitin, Chitosan and Related Enzymes*, (Academic Press, Inc., New York, 1984).
Audus and Borchardt, *Bioreversible Carriers in Drug Design*, 27–47, (E. B. Roche, Pergamon Press, New York, 1986).
Audus and Borchardt, *Am. J. Pathol.*, 103, 353–366 (1981).
Gallo and Hassan, *Pharm. Res.*, 5, 300–304, (1988), (not prior art).

*Primary Examiner*—C. Fred Rosenbaum
*Assistant Examiner*—Sharon Finkel
*Attorney, Agent, or Firm*—Kilpatrick & Cody

[57] ABSTRACT

A delivery system for biologically active materials consisting of polysaccharide or polypeptide microspheres which bind to glycosaminoglycan receptors on cell surfaces. The delivery system can be used to localize drugs by both biochemical and physical means. In one embodiment, microspheres prepared from the polysaccharide chitosan are bound to anionic polysaccharides similar to the glycosaminoglycan receptors found on the surface of capillary endothelial cells. The microspheres were formulated to have a controlled cationic character, and had a mean diameter of 0.70 u and a magnetite content of 16% w/w. Binding to a model polysaccharide, heparin, was demonstrated in vitro. Binding to cultured cerebral capillary endothelial cells was also demonstrated.

3 Claims, 2 Drawing Sheets

RECEPTOR-MEDIATED DELIVERY SYSTEM

This is a continuation of U.S. Ser. No. 07/188,358, filed on Apr. 29, 1988, by James M. Gallo and Emad E. Hassan now abandoned.

BACKGROUND OF THE INVENTION

This invention relates to controlled delivery systems targeted to polysaccharide molecules on cell surfaces.

A targeted drug delivery system is most often a drug associated with a macromolecule or particulate carrier, designed to be localized at a specific anatomic region in the target site. Recently, there has been a greater focus on utilizing receptor-mediated carriers, such as monoclonal antibodies, that interact with cell surface receptors at the drug's intended site of action.

An apparent limitation of this type of system is that, following intravascular administration, a large fraction of the carrier may never reach an extravascularly located target site due to the systemic distribution via the blood circulation. There is nothing inherent in the design of these drug carrier systems that will enable the carrier to be localized in the capillaries of the target site.

An alternate approach is to utilize carriers that have receptors on the capillary endothelial cells. This idea has been recently expressed by Ausprunk and Borchardt, *Am. J. Pathol.* 103,353–366 (1981), with respect to targeting drugs to the brain. They suggest the use of carriers that could be transported across the blood-brain barrier by specialized transport processes (i.e., amino acids), or by receptor-mediated transcytosis (i.e., as suggested for insulin).

It is therefore an object of the present invention to provide a receptor-mediated carrier system for the directed, controlled delivery of biologically active compounds to specific types of cells, such as brain cells.

It is a further object of the present invention to provide a method for making a receptor-mediated carrier system for the controlled delivery of compounds which is relatively easy, uses safe materials, and economically feasible.

It is a still further object of the present invention to provide a receptor-mediated carrier system for the directed, controlled delivery of biologically active compounds to specific types of cells which is flexible but relatively specific.

SUMMARY OF THE INVENTION

Cationic carriers are designed to bind to glycosaminoglycan (GAG) receptors located on the surface of capillary endothelial cells. The GAGs are polysaccharides such as heparan sulfate and chondroitan sulfate and are discretely distributed on the plasma membrane. Heparan sulfate is particularly concentrated at the luminal aspect of the fenestral diaphragm. Magnetic chitosan (poly(1->4)-D-glucosamine) microspheres were prepared and demonstrated to bind to heparin, a model glycosaminoglycan in solution, and cultured cerebral capillary endothelial cells of bovine origin as an example of a novel targeted drug delivery system utilizing polysaccharide or polypeptide microcapsules which bind to glycosaminoglycan receptors on cell surfaces.

Because the GAG receptors participate in cellular events such as receptor-mediated transcytosis and regulation of coagulating-anticoagulating systems, it is believed that these polysaccharide microspheres, having biologically active substances bound to or encapsulated within, can be used to effect controlled, targeted, or enhanced, drug delivery to cells bearing these receptors.

2, absorbance following chitosan additions to the saturated methylene blue:heparin complex.

Figure 2:
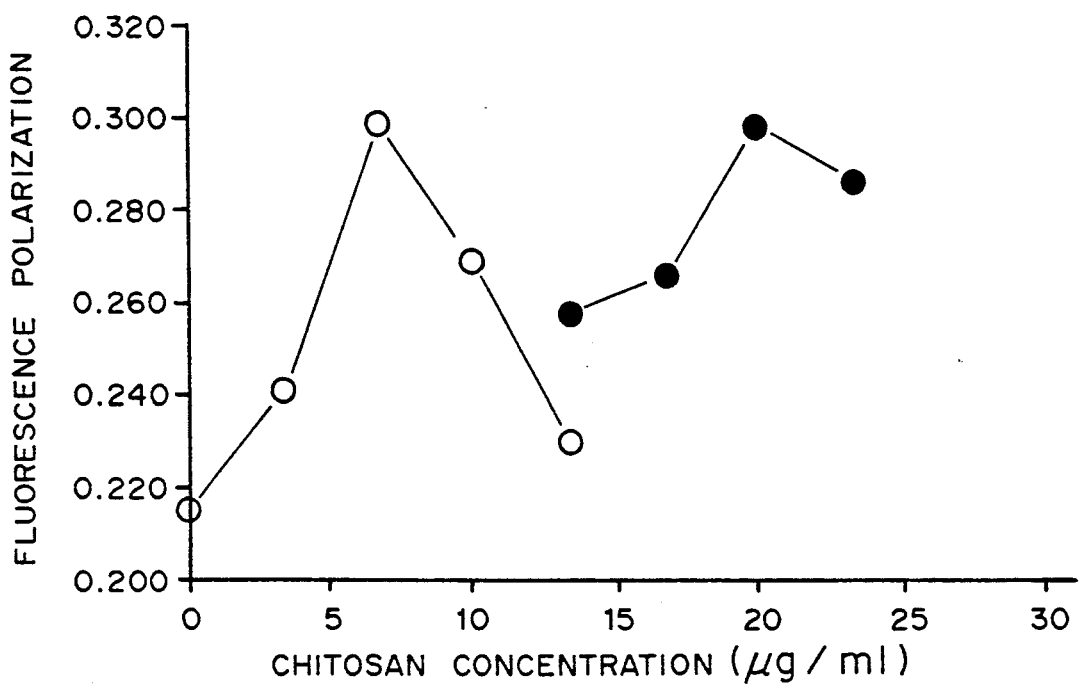

FIG. 2 is a graph of fluorescence polarization as a function of chitosan concentration (2.8 ml of 0.066 $\mu$g/ml FLC plus 0.2 ml endothelial cell suspension, first curve, plus an additional 0.2 ml endothelial cell suspension, second curve).

Figure 3:
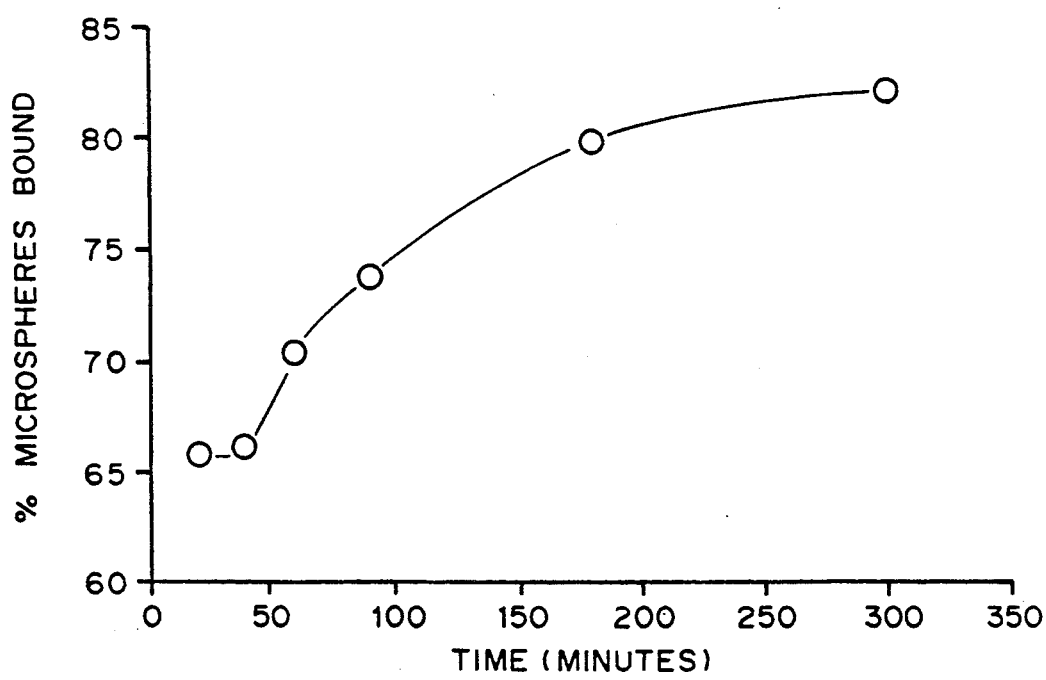

FIG. 3 is a graph of the % microspheres bound over time to cerebral endothelial cell monolayers (0.8 ml of microsphere suspension equivalent to a chitosan concentration of 75 $\mu$g/ml).

DETAILED DESCRIPTION OF THE INVENTION

The present invention is a novel approach to drug delivery using receptor-mediated carriers. In the preferred embodiment, magnetic particles are included so that, under the influence of a suitable magnetic field, the magnetic particles will be stationary, thereby enhancing binding of the carrier to the capillary endothelial cell receptors. The retained magnetic microspheres may then be taken up by endocytosis and by passage through adjacent endothelial cell gaps in fenestrated or discontinuous capillary beds. In continuous capillary beds, i.e., the blood-brain barrier, the receptor-mediated binding of the particle to the capillary wall may create a local concentration gradient as drug is released from the particle. The concentration gradient may lead to increased brain concentrations for drugs permeable to the blood-brain barrier.

The basis for this capillary endothelial receptor-mediated delivery system is the formation of a complex between the anionic heparin-related glycosaminoglycans on the luminal surface of the capillary endothelial cells and cationic magnetic microspheres. A strong interaction between cationic microspheres and anionic glycosaminoglycan receptors should retain the microspheres in the capillary region. Other polymers which exhibit similar interactions with glycosaminoglycan receptors could be utilized in place of the polysaccharides, such as some of the polypeptide lectins.

EXAMPLE 1

Preparation of Magnetic Microspheres and Analysis of Binding to Polysaccharide

Cationic magnetic microspheres were prepared from approximately 83% deacetylated chitin, herein referred to as chitosan. Chitin (poly(1->4)N-acetyl-D-glucosamine), and its deacetylated derivative, chitosan, are naturally-occurring polysaccharides.

MATERIALS AND METHODS

Chemicals

Chitosan, low viscosity grade (M.W. 652,000) was purchased from Proton Laboratories, Redmond, Wash. The following were obtained from Sigma Chemical Co., St. Louis, Mo.; sorbitan sesquioleate (Arlacel 83, S3386), bovine serum albumin (A-7030), methylene blue (MB1) and heparin sodium (from porcine intestinal mucosa, H7005). Ferrofluid (EMG IIII) was purchased from Ferrofluidics Corp., Nashua, N.H. Double-distilled deionized water was obtained from a Millipore (Bedford, Mass.) system. Extra heavy mineral oil was purchased from Ruger Chemical Co., Irvington, N.J. All other chemicals were analytical grade.

Equipment

The ultrasonic water bath was a Bransonic 220; the ultrasonic probe was a Branson Sonifier. A Brinkman Rotovapor-R vacuum drier was used. All absorbance data were obtained from a Varian 2200 Spectrophotometer. Iron analyses were completed with a Perkin-Elmer 5000 atomic absorption spectrophotometer. A philips 505 scanning electron microscope was used for particle size analysis.

Preparation of Magnetic Chitosan Microspheres

One hundred and fifty milligrams of chitosan were dissolved in 6 ml of 10% (v/v) acetic acid in deionized water. To this solution, 4 ml of acetone were added and the contents vortexed until a clear solution was obtained. In a 75 ml double-walled beaker, one milliliter of chitosan solution was sonicated with 100 $\mu$l of a 10% (w/v) ferrofluid suspension in a water bath for 10 min. To this mixture, 50 ml of mineral oil was added, and an emulsion was formed by sonication for 3 min at 200 W with an ultrasonic probe. The temperature of the emulsion was controlled with a circulating water system maintained at 4° C. 100 $\mu$l of Arlacel 83 was then added to the emulsion as a stabilizer. The emulsion was then placed in a rotary vacuum drier under nitrogen atmosphere at 70° C. for 2 hrs to evaporate the acetone and water in the internal phase. Following evaporation, the microsphere suspension was diluted with 60 ml of hexanes containing 1% v/v Arlacel 83 and centrifuged at 4500 RPM for 15 min. The supernatant was decanted and the microsphere pellet was washed twice in 80 ml of hexanes containing the Arlacel 83. The solid microsphere pellet was then suspended in 15 ml of anhydrous ether and transferred with two 300 G bar magnets in place to a 20 ml centrifuge tube to retain any free magnetite. After centrifugation at 2000 RPM for 5 min, the ether was removed and the microspheres were stored at room temperature.

The method of magnetic chitosan microsphere preparation is similar to techniques used for magnetic albumin microspheres. The primary difference is that solid chitosan microspheres are obtained by solvent evaporation rather than by protein denaturation of the emulsion. The nitrogen atmosphere increased both the rate of solvent evaporation and the stability of the microspheres. Arlacel 83 was added to prevent breaking of the emulsion at temperatures above 50° C. The surfactant also increased the recovery of the microspheres by preventing their adhesion to glass surfaces. Approximately 10 mg of microspheres were recovered per batch.

Particle Size Analysis

Particle size analyses were done with a scanning electron microscope. Approximately 600 $\mu$g of the microspheres were digested in 1 ml of concentrated hydrochloric acid for 12 hrs and the magnetite content of the microspheres was obtained from atomic absorption spectroscopy. The samples were diluted 20 times with deionized water and measured for iron at a wavelength of 248.3 nm.

Numerous batches of microspheres were prepared by the above method. It was found that the mean particle diameter was $0.70\mu = / - 0.20\mu$ (n=350). The magnetite ($Fe_3O_4$) content of the microspheres was 16% w/w $\pm 2\%$ (n=4).

Chitosan-Heparin Complexation Studies

The chitosan:heparin complex was studied on the basis of the competitive binding displacement method, using methylene blue as the competing marker.

The following solutions were prepared: 570 $\mu$g/ml of methylene blue in deionized water (MB1), 5.7 $\mu$g/ml of methylene blue in 1% v/v acetic acid in deionized water (MB2), 2.25 mg/ml of heparin in deionized water (H), 2.25 mg/ml of chitosan in 1% v/v acetic acid in deionized water (C), and 2.25 mg/ml of bovine serum albumin in deionized water (BSA). The pH of 1% v/v acetic acid in deionized water was 3.5.

The following solutions were mixed in stoppered vials: 1 ml of H and 9 ml of MB2; 0.1 ml of MB1, 7.9 ml of 1% v/v acetic acid, 1 ml H and 1 ml C; 0.1 ml MB1, 7.9 ml 1% v/v acetic acid, 1 ml H and 1 ml BSA. The visible absorbance spectrum was obtained for each mixture between 520 nm to 700 nm with 1% v/v acetic acid in the reference cell. Spectra of MB1 and ten-fold dilutions of H, C, and BSA in 1% v/v acetic acid were also obtained.

The interaction between heparin and the magnetic chitosan microspheres was also studied by the competitive binding displacement method. A mixture of 0.1 ml H, 0.1 ml MB1, 9.8 ml of deionized water (pH=7) and 4 mg of magnetic chitosan microspheres was prepared and the absorbance scan was recorded. An exactly analogous mixture was prepared with alkali treated microspheres obtained after mixing the magnetic chitosan microspheres with 2% v/v ammonium hydroxide in acetone for 10 min. The basic treatment was used to neutralize the ammonium ions on the chitosan molecules.

Characterization of the complex ratio was completed as follows. To 0.1 ml of MB1, volume increments of a 0.225 mg/ml heparin solution was added. After each volume addition of heparin, 1% v/v acetic acid in deionized water was added to obtain a final volume of 15 ml. The absorbance of the resulting solution was recorded at 660 nm. In a second study, a 0.225 mg/ml chitosan solution was added in volume increments to the methylene blue:heparin complex (0.1 ml of MB1 and 1.5 ml of 0.225 mg/ml heparin). The resulting mixture was diluted to 15 ml with 1% v/v acetic acid, and the absorbance measured at 660 nm.

Due to the heterogeneity of the heparin polymer, the chitosan:heparin complex ratio calculation was based on a heparin tetrasaccharide with a molecular weight of 1026 daltons. The corresponding molecular weight of the chitosan tetramer was 632 daltons.

Figure 1:
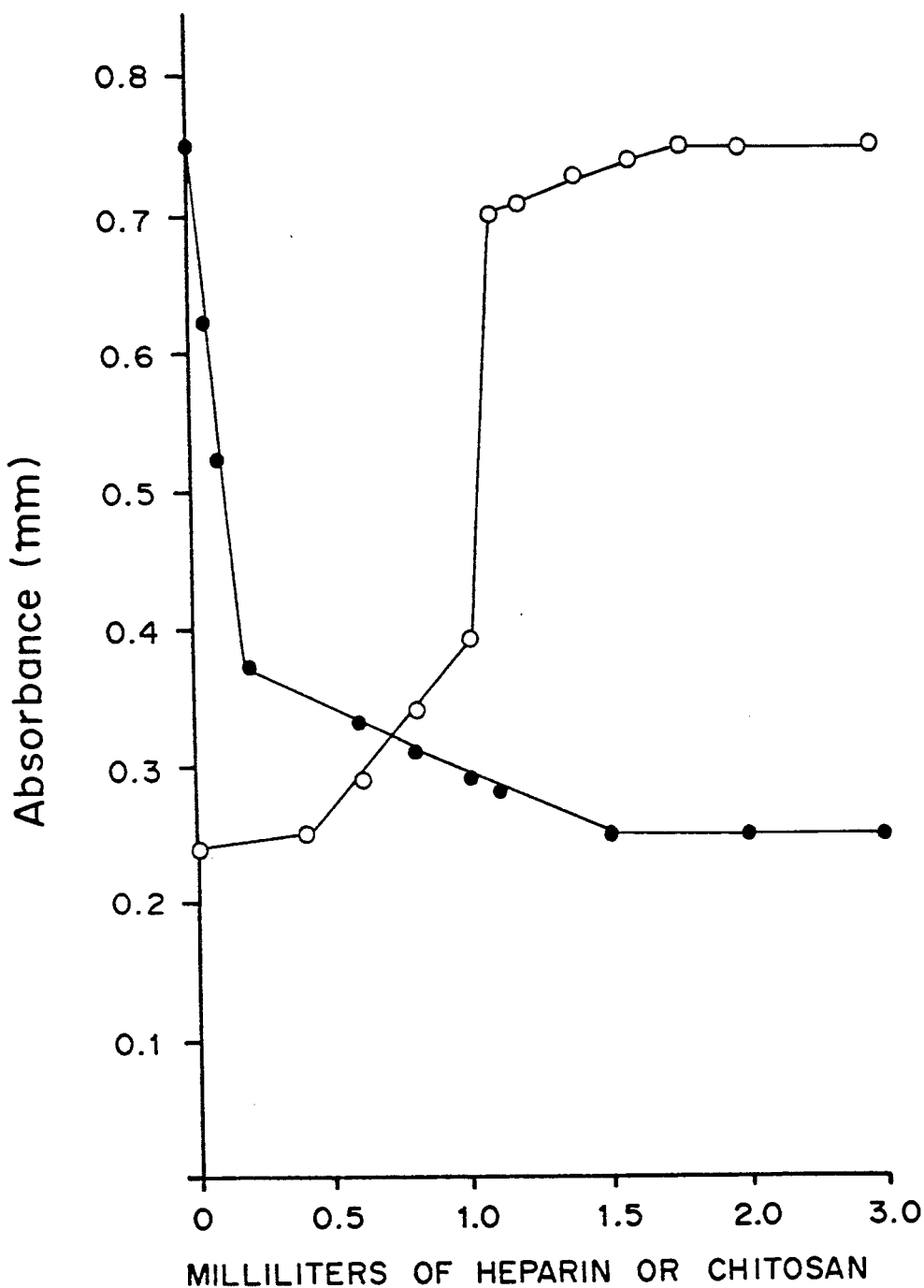
FIG. 1 is the absorbance as a function of either heparin or chitosan addition to heparin-chitosan mixture, demonstrating heparin-chitosan complex formation: 1, absorbance following heparin additions to methylene blue.

The absorbance spectra from the complex studies indicates the formation of a complex. Addition of chitosan to the heparin:methylene blue complex produced the methylene blue spectrum, indicating the formation of a chitosan:heparin complex. Bovine serum albumin did not affect the absorbance spectrum of the methylene blue:heparin complex. Similar to the results for the addition of chitosan to the heparin:methylene blue complex, the magnetic chitosan microspheres displaced methylene blue from heparin binding sites causing the methylene blue spectrum to be regenerated. The methylene blue:heparin spectrum remained the same after the addition of the alkali-treated microspheres, indicating that a complex was not formed between alkali-treated microspheres and heparin. As shown in FIG. 1, the addition of heparin causes the absorbance to decrease, a hypochromic effect, indicating that methylene blue is being bound to heparin. The slower decline in absorbance most likely represents rearrangement of methylene blue molecules on heparin binding sites. The curve reaches a plateau when all methylene blue is bound to heparin. Addition of chitosan to the methylene blue:heparin complex causes an increase in absorbance consistent with methylene blue's displacement from heparin binding sites. The sharp increase in absorbance represents the complete displacement of methylene blue from heparin binding sites by chitosan. The small increase in absorbance prior to the plateau region of the curve is most likely due to polymer-dye interactions. The chitosan:heparin complex ratio was determined to be 1:1 based on charge.

The magnetic chitosan microspheres were less than one micron in diameter, allowing distribution to capillary endothelial cells following intravascular administration. The magnetite content of 16% w/w should be sufficient to retain the particles at capillary blood flow rates under the influence of a suitable magnetic field. The amount of magnetite which can be utilized can be varied, however, optimizing as desired using techniques available to those skilled in the art.

Heparin was used as a structural analogue for the glycosaminoglycans. Since the cationic moiety of methylene blue attacks anionic heparin binding sites, the competitive binding displacement method is valid to study the chitosan:heparin complex. A polylysine:heparin complex has been extensively studied and a chitosan:heparin complex has been observed, both complexes indicative of macromolecular ion complexes. The reaction between chitosan and heparin was studied at an acid pH in which chitosan is soluble. The similar spectra obtained from the methylene blue:heparin complex and following the addition of albumin indicate that albumin does not specifically bind to anionic sites on heparin. Thus, albumin microspheres should not interact with glycosaminoglycan receptors at ionic binding sites.

The complex formed between the magnetic chitosan microspheres and heparin was formed in deionized water at pH 7. At this pH, $SO_3^-$ and $COO^-$ groups are present on heparin and will complex with ammonium ions on the microspheres. A physiological pH of 7.4 could not be used since methylene blue is not ionized at pH values above 7, thus preventing the formation of a methylene blue:heparin complex. Chitosan is insoluble at pH 7 but ammonium ions are apparently present due to the association of the acetic acid with the microspheres. Acetic acid is used in the formulation of the microspheres to dissolve the polymer prior to emulsification, and may also serve to control the ionization of the amino group on the chitosan molecule. The association of the acetic acid with the microspheres will provide a local acid environment in vivo to facilitate microsphere binding to the glycosaminoglycan receptors. The cationic:anionic nature of the microsphere:heparin complex is supported by the fact that neutralized microspheres did not displace methylene blue from heparin. The neutralization procedure will produce ammonium acetate and water and make available free amino groups on chitosan.

It is thought that the ionic and hydrogen bonding forces between the chitosan microspheres and the glycosaminoglycans on the capillary endothelial cells will be sufficient to retain the microspheres in the capillaries. Heparan sulfate proteoglycans are considered to form microdomains on capillary endothelial cell surfaces, and are involved in endocytotic and transcytotic events. Heparan sulfate proteoglycans are involved in the receptor-mediated uptake of low-density lipoproteins. Thus, binding of chitosan microspheres to glycosaminoglycans should result in endocytosis in peripheral capillary beds. Further, the carrier:receptor complex may trigger the receptor-mediated endocytosis of the glycosaminoglycans. This later process is a normal turnover mechanism for damaged or aged glycosaminoglycans on the cell surface. The complex of polylysine:heparin is taken up at a greater rate than the unassociated species into hamster ovarian cells.

EXAMPLE 2

Binding of Chitosan and Chitosan Microspheres to Endothelial Cell Monolayers.

Methods

Preparation of cultured endothelial cells

Cerebral bovine microvessel endothelial cells were isolated from the gray matter of the cerebral cortex and cultured according to the methods of Audus and Borchardt. Endothelial cells were grown on 35 mm plastic culture dishes and homogenous monolayers were obtained 10–14 days after seeding. The protein content of cultured endothelial cells was determined using the Biorad-Bradford protein assay. Cells were digested with 1.8 ml 2N sodium hydroxide for two hours prior to protein assay. Bovine serum albumin was used as the standard.

Binding of molecular chitosan to endothelial cell suspension

The cultured endothelial monolayers were washed with serum free culture medium followed by pH 7.4 phosphate buffered aline (PBS), three times each. Each monolayer was incubated with 2 ml 0.1% collagenase in PBS for 10 minutes at 37° C. Cells were gently scraped by a rubber policeman and transferred to a 15 ml centrifuge tube. Cells were separated by centrifugation at 1000 rpm and washed twice with serum free culture medium followed by two washes with PBS. The final pellet was resuspended in PBS to yield a protein concentration of 38.2 μg/ml.

All fluorometric titrations were measured with spectrofluorometer at an excitation wavelength of 495 nm and an emission wavelength of 530 nm. The fluorescence polarization of increasing concentrations of fluorescein labeled concanavalin A were measured in the presence of a 3.3 μg/ml chitosan solution, 1% acetic acid, and in PBS. Fluorescence polarization measurements were also obtained by titration of three mls of 0.066 μg/ml fluorescein labeled concanavalin A solution with 1% acetic acid, 1 mg/ml chitosan solution in 1% acetic acid and the endothelial cell suspension. To study the chitosan-endothelial cell interaction, 0.2 ml of cell suspension and 2.8 ml of 0.06 μg/ml fluorescein labeled concanavalin A in PBS were stirred with a magnetic stirrer for five minutes then titrated with 10 μl increments of a 1 mg/ml chitosan solution. Steady-state fluorescence polarization were directly recorded after each addition of titrant. AFter addition of the fourth increment of the chitosan solution, 0.2 ml of cell suspension was added and the titration was continued.

Binding of chitosan microsphere to endothelial cell monolayers

Chitosan magnetic microspheres were prepared as above and suspended in 10 mM PBS just before use. The prepared endothelial cell monolayers were washed with three portions of 2 ml of PBS after aspiration of the culture medium. 0.8 ml of freshly prepared microsphere suspension equivalent to a chitosan concentration of 75 µg/ml was then added to each washed monolayer and incubated undisturbed at 37 C. in an atmosphere of 5% $CO_2$ and 95% humidity. After 20, 40, 60, 90, 180 and 300 minutes of incubation, the percentage of unbound chitosan microspheres was determined as follows: the microsphere suspension was poured into a 10 ml centrifuge tube and the monolayer was washed three times by adding 1 ml of PBS, swirling for one minute and then pouring the wash medium into the 10 ml centrifuge tube. Any remaining washing buffer in the dish was then collected by aspiration and combined with the other washings in the 10 ml centrifuge tube. The tube was then centrifuged at 2000 rpm for 30 min to collect the unbound microspheres. The microsphere pellet was dissolved in 1% acetic acid and assayed for chitosan using the colormetric method of Ride and Drysdale Physiol.Plant.Path. 2,7–15 (1972). The fraction of microspheres bound to the cells was calculated as the difference between the initial amount of chitosan (added as microspheres to the cells) and the amount of chitosan recovered from the washes (due to unbound microspheres) divided by the initial amount of chitosan.

The above procedure was also used to examine the effect of heparin and ruthenium red on the binding characteristics of chitosan magnetic microspheres to endothelial cell monolayers. Microspheres were suspended in PBS containing 250 µg/ml heparin or ruthenium red. Unbound microspheres were collected, the chitosan concentration determined, and the fraction of microspheres bound in the presence of heparin and ruthenium red was calculated as described above.

The chitosan concentration (as microspheres) was 36.3 µg/ml in the PBS control and in the presence of heparin and 45.7 µg/ml in the presence of ruthenium red.

Fluorescein labeled concanavalin A was used as a surface marker to cerebral endothelial cells because concanavalin A binds to specific carbohydrate receptors on cell membranes (glucose and mannose containing domains). It has also been shown that concanavalin A binds to rat heart capillary endothelial cell surfaces. This binding is reversible and could be inhibited by methyl-D-mannoside. Concanavalin A remains at cell surfaces for at least four hours before it is transferred into the cell.

Changes in fluorescence polarization of increasing concentrations fluorescein labeled concanavalin A (FLC), in the presence of molecular chitosan, acetic acid or PBS was measured. The decrease in FLC polarization in the chitosan and acetic acid media compared to the PBS medium indicated a lack of interaction between chitosan and FLC. Thus, any increase in fluorescence polarization upon addition of chitosan to the endothelial cell suspension marked with FLC is solely due to binding of chitosan to cell surfaces.

When FLC solution was titrated with endothelial cell suspension, fluorescence polarization was increased as a result of binding of FLC to the endothelial cell surface. FIG. 2 shows the fluorescence polarization of cell suspension marked with FLC in the presence of chitosan. Upon increase of the chitosan concentration an increase in fluorescence polarization occurred as a result of the binding of chitosan to the cell surfaces. After reaching a peak, the fluorescence polarization decreased. The decrease in polarization at high chitosan concentrations may be due to the release of FLC from cell surfaces by chitosan molecules. This possibility is supported by the fact that addition of more cell suspension followed by continuing titration with chitosan solution leaded to a curve with the same characteristics as the previous one.

The binding of chitosan magnetic microspheres to endothelial cell monolayers, expressed in terms of the percentage of bound microspheres, is illustrated in FIG. 3. The percentage of microspheres bound to the monolayers increased with an increase in the incubation time, reaching a maximum of 81.9% after five hours. This plateau value apparently represents the microspheres saturating the glycosaminoglycan receptors on the cell surface. The time dependency of the percentage of microspheres bound is probably due to the time required for the microspheres to sediment to the cell monolayer.

Both heparin and ruthenium red inhibited the binding of the chitosan microspheres to the cultured monolayers. Heparin sharply decreased the percentage of bound microspheres to 33%, as compared to 80.7% in PBS. Heparin inhibited the binding of the microspheres to the cell surface glycosaminoglycan receptors by occupying chitosan binding sties, supporting the idea that the microspheres primarily bind to the glycosaminoglycans through ionic interactions. As shown in example 1, heparin and chitosan form an anionic:cationic complex through $SO_3$ and $COO$ and $NH_3^+$ groups. Ruthenium red is a cationic dye which binds to anionic domains of cell membranes (e.g. sialoglycoconjugates and glycosaminoglycans). The partial inhibition of microsphere binding due to ruthenium red is therefore indicative of interactions between the chitosan microspheres and endothelial cells through the glycosaminoglycan receptors.

In conclusion, polysaccharides such as chitosan, either in solution or as magnetic microspheres, bind to cerebral microvessel endothelial cell surfaces. The binding is mediated by anionic glycosaminoglycan receptors. Other polysaccharides and polypeptides such as lectins can be used to form similar drug delivery systems, using the above-described methods. These systems should have a number of applications in controlled drug delivery, especially to hard to reach areas such as the brain.

Modifications and variations of the present invention, a drug delivery system utilizing microcapsules which bind to glycosaminoglycan receptors on the surface of cells, will be obvious to those skilled in the art from the foregoing detailed description of the invention. Such modifications and variations are intended to come within the scope of the appended claims.

We claim:

1. A drug delivery system, comprising a cationic polysaccharide microsphere having an average diameter of less than one micron, a drug releasably bound to the polysaccharide, and a sufficient amount of magnetic material to permit any movement of said microsphere to be controlled by a magnetic field, wherein said cationic microsphere binds to anionic glycosaminoglycan cell surface receptors by ionic interaction.

2. The system of claim 1 wherein the drug is bound to the microspheres.

3. The system of claim 1 wherein the drug is encapsulated within the microspheres.

* * * * *